United States Patent
Gomez Rabago

(10) Patent No.: US 12,036,318 B2
(45) Date of Patent: Jul. 16, 2024

(54) SELF-EMULSIONABLE MINERAL OIL AS A VEHICLE IN VACCINES FOR POULTRY

(71) Applicant: CHEMICAL & SCHUTZ HIGH PERFORMANCE LUBRICANTS, S.A. DE C.V., Aguascalientes (MX)

(72) Inventor: Bernardo Gomez Rabago, Aguascalientes (MX)

(73) Assignee: CHEMICAL & SCHUTZ HIGH PERFORMANCE LUBRICANTS, S.A. DE C.V., Aguascalientes (MX)

( * ) Notice: Subject to any disclaimer, the term of this patent is extended or adjusted under 35 U.S.C. 154(b) by 99 days.

(21) Appl. No.: 17/673,315

(22) Filed: Feb. 16, 2022

(65) Prior Publication Data

US 2023/0255886 A1 Aug. 17, 2023

(51) Int. Cl.
*A61K 9/107* (2006.01)
*A61K 39/39* (2006.01)

(52) U.S. Cl.
CPC .............. *A61K 9/107* (2013.01); *A61K 39/39* (2013.01)

(58) Field of Classification Search
None
See application file for complete search history.

(56) References Cited

U.S. PATENT DOCUMENTS

| 2012/0321663 | A1  | 12/2012 | Bertrand et al. |
| 2015/0196487 | A1* | 7/2015  | Detraz ................... A61K 39/39 424/234.1 |
| 2016/0220659 | A1* | 8/2016  | Audonnet ................ C12N 7/00 |
| 2022/0211844 | A1* | 7/2022  | Ban ........................ A61K 9/107 |

FOREIGN PATENT DOCUMENTS

| CN | 5-255112    |   | 10/1993 |
| CN | 102579339   | * | 7/2012  |
| CN | 102579339 A | * | 7/2012  |
| CN | 108014332   |   | 5/2018  |
| CN | 108159414   |   | 6/2018  |
| FR | 2 017 251   |   | 5/1970  |
| MX | 319213 B    |   | 4/2014  |

OTHER PUBLICATIONS

GE Chem (2003) (Year: 2003).*

* cited by examiner

*Primary Examiner* — Celeste A Roney
(74) *Attorney, Agent, or Firm* — HSML P.C.

(57) ABSTRACT

The present invention relates to a self-emulsionable mineral oil used as a vehicle in poultry vaccines, and a method for producing self-emulsionable mineral oil, comprising the steps of: placing paraffinic mineral oils in a container with stirring; shake until a homogeneous mixture is obtained; without suspending stirring, add adjuvants on the homogeneous mixture; and continue stirring until a homogeneous mixture is obtained.

14 Claims, 5 Drawing Sheets

SELF-EMULSIONABLE MINERAL OIL AS A VEHICLE IN VACCINES FOR POULTRY

FIELD OF THE INVENTION

The present invention refers to a self-emulsionable mineral oil used as a vehicle in poultry vaccines, and a method to produce it.

The present invention relates to the use of reagents in the formulation of the manufacture of vaccines for use in the poultry industry in the prevention of diseases of viral origin that seriously affect this animal species; such as Newcastle Disease, Avian Influenza disease, and Infectious Bronchitis, among many others.

The present invention promotes vaccines to stimulate the different immunological mechanisms of birds, providing an efficient response regarding protection against the challenge of virulent or fields virology, as represented in Mexico and other countries of the world by Newcastle Disease and Avian Influenza.

BACKGROUND OF THE INVENTION

Poultry production is a very important livestock activity in Mexico, by considering that it has a per capita production of 25 Kg of eggs per year, representing the first place in the world for consumption of this product and chicken with 3.7 million tons per year with a growth of 3%. In this activity, one of the great risks in infectious diseases caused by viruses such as Avian influenza, Newcastle disease, Infectious Bronchitis, Infectious bursal disease (IBD) (also known as Gumboro disease, infectious bursitis, and infectious avian nephrosis), posture loss syndrome and others.

Newcastle disease Virus (NDV) is a viral infection that affects domestic hens, canary, turkeys, pigeons, and other birds. It is characterized by the presence of high mortality and morbidity with respiratory, digestive, and nervous signs. It is caused by a *paramyxovirus*. It is considered to be a calamitous disease and the most feared by poultry farmers.

Newcastle disease has been known since 1926, when the first outbreak was recorded on the island of Java, Indonesia, and shortly thereafter in the Newcastle region, United Kingdom. Later, it appeared in Europe, Asia, and the United States. During World War II, the NDV spread to most of the world. Despite the efforts made since the 1950s to control and eradicate the disease, it is still considered today as a panzootic, endemic in many countries, although it occurs sporadically in others.

In Mexico, the NDV is one of the main diseases that affect poultry, causing economic losses to the poultry industry, backyard chickens, and gamecocks. Outbreaks of this disease occur at any time of the year, but most often in late winter and spring.

The taxonomic position of the Newcastle Disease virus (NDV) within the family was changed from the Genus *Paramyxovirus* to the Subfamily Paramyxovirinae, Genus *Rubulavirus*. However, recently the information on the nucleotide sequence of the NDV shows that it is more closely related to the members of other genres in that subfamily, the paramyxoviruses and the morbilliviruses than they are to that of the rubella viruses in which the Rubiola viruses make up the type species.

The incubation period for NDV can be from 5 to 12 days in chickens, turkeys, and pigeons.

There are two ways of transmission:

a) Direct transmission, the infection occurs by direct contact through aerosols, from bird to bird. Direct contact with the secretions of sneezing, lacrimation, vaccinated birds, and carrier birds, by aerosols or drops that susceptible birds inhale. By direct contact with excretions, they expel large amounts of virus in the feces; this appears to be the main method of dissemination from bird to bird and through contact with dead bird organs, contaminated food, or water.

b) Indirect transmission, through fomites (equipment, vehicles, etc., contaminated with the virus). Relocation of live birds, personnel, poultry products, also artificially created conditions such as ventilation in intensively managed poultry houses, wild birds by infection or mechanical transfer. Broken eggs or feces with the virus contaminate the outside of the eggs.

Morbidity in chickens and turkeys is variable, depending on the resistance of the birds and the virulence of the virus strain. This factor plays an important role in animal management and immunosuppression states. However, it is considered high as affected animals stop eating, lose weight, which are secondary agents that are associated to complicate the clinical picture.

Mortality is generally high and depends on the strain of the virus.

Four types of strains are known:

1) Apathogenic, those viruses infect birds without causing clinical signs, and upon inoculation into embryos, the virus replicates without causing embryonic death.
2) Lentogenic, those viruses that in birds cause slight clinical signs without mortality and in embryos inoculated with this type of virus can cause mortality after 110 hours. In the intracerebral inoculation in chickens, they do not replicate. They generally strain for vaccine use.
3) Mesogenic, those viruses that cause clinical signs and mortality of 30 to 60% and have the property of killing embryos after 72 hours and do not replicate in the nervous tissue of chicks inoculated intracerebrally.
4) Velogenic, those viruses that cause signs and high mortality of up to 100% and can kill the inoculated embryo within 72 hours. Inoculation of these strains intracerebrally into chicks causes death.

Currently, 5 different strains have been identified in terms of their form of clinical manifestation or pathotypes:

1) Velogenic viscerotropic, a very virulent virus with high mortality in birds of any age with lesions only in the digestive system.
2) Velogenic neurotropic, virus strain that causes respiratory and nervous signs with high mortality.
3) Mesogenic, a virus that causes moderate mortality with respiratory and sometimes nervous signs.
4) Asymptomatic enteric, enteric strains without the presence of clinical picture.

The virus can enter through the oral, ocular, and nasal routes. The first replication takes place at the level of the respiratory, digestive, or conjunctival epithelium, hence the virus will continue its replication in lymphoid tissue mainly lymphocytes and macrophages to cause severe leukopenia. The second replication is carried out after passing into the blood through the lymphatic pathway causing viremia and fever, first in vascular endothelium to cause rupture of the endothelium and with this, hemorrhages with the formation of thrombi, later in parenchymal organs, tissue, and lymphoid organs and finally the brain. The virus is shed in high concentrations in secretions, feces, blood, and feathers.

According to the pathogenesis of the virus, the clinical signs can be diverse, everything will depend on the strain of virus present.

Four clinical forms of the disease can be observed: neurological, digestive, respiratory, and respiratory-nervous. It all depends on the strain that infects the birds.

Prevention is based on two concepts: the first in biosecurity applied to farms, and the second in the use of vaccines.

There are three types of vaccines commercially available:
Active virus of lentogenic and inactivated strains
Active virus of mesogenic strains
Active virus of Lentogenic strains.

The application of active virus vaccines with Lentogenic strains is recommended to be administered individually, with a drop in the eye or in the nostrils, it is time-consuming, but it is the most appropriate way to guarantee the immunization of the birds. There are other vaccination methods with this type of biological, such as in drinking water, it is more practical when the massive application is required in large populations of birds and the spraying of the vaccine with machines that generate aerosols, not recommended for gamecocks. The administration of Lentogenic vaccine strains allows the rapid vaccination of large numbers of birds and the immune response is rapid, the aerosols can penetrate deep into the respiratory system, producing reactions that can be serious in highly susceptible birds. Typical vaccine strains are Hitchner B1 and La Sota (wider use), Strains F and V4, such as Roakin, Mukteswar, Komarov, and H, are obtained from very virulent strains in the laboratory. Its common use is restricted in countries with very virulent viruses. The method of application varies depending on the strain, some are administered in drinking water while others require intradermal inoculation in the crease of the wing. They are capable of causing severe disease and should therefore only be used after primary vaccination with Lentogenic viruses.

These inactivated vaccines are prepared from viruses that replicate in chicken embryos, from which the viruses are harvested and inactivated by treatment with formalin or beta-propiolactone. Oils are used as adjuvants in inactivated aqueous vaccines. Immunogenicity can vary. It must be applied individually via I.M. or S.C. Birds must be vaccinated with the live virus when they are a day old with a drop in the eye or by aerosol to establish infection in some birds, which will spread it to others, followed by revaccination at 3 or 4 weeks, generally revaccination is performed with an inactivated virus vaccine with aluminum hydroxyl adjuvant or in oil suspension. Other companies vaccinate at the age of 9 to 12 days of age and apply the active virus vaccine in the eye and simultaneously the inactivated vaccine. In the case of replacement birds, polyvalent vaccines (various immunogens) are applied in oil suspensions at different ages.

In the manufacture of these biologics, it is very important to use different adjuvants that allow them to be mixed with the different immunogens (viral antigens) in order to increase the stimulus to the immune system of that individual whom it is intended to protect with the biological. that it is imperative to investigate and invent new reagents and formulas that help to increase the immune response, that is innocuous and safe to achieve the objective of the immunogen of interest.

Adjuvants are substances or reagents that accelerate, prolong or enhance the specific immune response against inoculated antigens. The word adjuvant comes from the Latin adjuvare, which means to help, to assist. Immunological adjuvants began to develop from the second decade of the 20th century, it was observed that horses that developed abscesses at the injection site of diphtheria toxoid generated higher titers of specific antibodies than those that did not have them. Subsequently, it was reported that abscesses generated by the injection of foreign substances together with the toxoid, increased the antitoxin response in horses. In 1926 the adjuvant activity of aluminum compounds was demonstrated by the use of a diphtheria toxoid vaccine precipitated in alumina. Today, aluminum adjuvants (aluminum phosphate and hydroxide) continue to be the most widely used immunological adjuvants and the only ones present in vaccines permitted in biologics for human use in the United States.

In this field, efficacy is of great importance and certain levels of side effects are tolerated. The most widely used adjuvants in veterinary vaccines are mineral oil emulsions (of the oil-in-water or water-in-oil type) and adsorbents (aluminum hydroxide and phosphate). In some cases, liposomes, saponins, vitamin E, immunostimulating complexes (ISCOM) are used, as well as different emulsions of oils of vegetable or animal origin. Although mineral oil emulsions, especially those of the water-in-oil type, induce a strong immune response, they can cause risks and unwanted effects, possibly due to their limited biodegradability and biocompatibility in cellular metabolism.

It is for this reason that numerous attempts have been made to develop effective and safe adjuvants. An example of this is the formulation composed of synthetic sulfo lipopolysaccharides, with hydrophobic characteristics, incorporated into an emulsion of squalene in water, developed by the Belgian company Solvay SA. This adjuvant has been successfully validated in laboratory animals with protein and viral antigens and is at least as effective as the mineral oil-based adjuvants used today in various veterinary vaccines.

In Mexico, the use of vaccines is regulated by the Official Mexican Standards (NOM) whose purpose is to comply with those requirements that guarantee their safety, innocuousness, and efficacy when used in animals, to meet these objectives the biological and pharmaceutical are subjected to verification tests such as the Purity, Sterility, Safety, Concentration or Titer, Efficacy or Challenge test, as well as the stability of the products.

In the production of pharmaceutical vehicles for the application of vaccines, it is known of pharmaceutical vehicles that present different disadvantages attributable to the formulation and the materials for the production of these, for example, mineral oils without adjuvants, oils with less stability to the emulsion, a lower antigenic spectrum in monovalent or bivalent vaccines, lower resistance to mishandling of the biological, namely, loss of the cold chain, deficiency in controlled release, and less protection in the application of vaccines, which decreases the creation of antibodies after the application of vaccines.

The document CN108014332 describes a veterinary vaccine adjuvant, comprising, by weight, 83.5% to 87.5% mineral oil, 3.5% to 4.5% Tween-80, 2.5% to 3.5% Span-80, 2.5% to 3.5% of propylene glycol, 2% to 2.5% of polyvinyl acid and 2% to 2.5% of glycerol monooleate. The document further discloses that the adjuvant helps the vaccine to have good stability and few side reactions and can provide stable long-term immunological protection.

The document JPH05255112 discloses an adjuvant composition having high adjuvant activity, comprising (A) a mineral oil such as bayol-F, drakeol or official paraffin, (B) a C4-10 cyclic dimethylpolysiloxane, (C) ethyl alcohol and (D) fatty acid ester of a polyhydric alcohol such as mannitol monooleate, sorbitan monooleate, sorbitan sesquioleate or condensed ricinoleate ester of hexaglycerol, preferably a surfactant having an HLB≥5, preferably in an A:B weight ratio:C:D from 5 to 70:5 to 70:1 to 30:1 to 15, as essential components. The adjuvant composition has suitable viscosity characteristics for inoculation and good keeping ability when used as a vaccine in animals.

The document FR2017251 discloses a vaccine against dead foot-and-mouth disease virus that is present in the form of a water-in-oil emulsion (virus in aqueous phase) containing 2 to 25% water and a water-in-oil emulsifier, preferably Mannide or sorbide monooleate, in an amount such that the emulsion is stable. The oil used is refined mineral oil. The advantages of the vaccine are that it provides a sustained release of antigen (over a period of 1 year or more under favorable circumstances) and has a low viscosity (which allows a relatively quick injection).

The document MX319213B discloses a method for preparing a vaccine composition that is used in a locally administered treatment against an avian viral disease, comprising at least the step of: a) mixing a vaccine, comprising at least one live virus selected from a virus belonging to one or more strains of avian disease, with an adjuvant diluent (AD), characterized in that the adjuvant diluent is an emulsion of the continuous aqueous oil-in-water phase or an oil-in-water microemulsion and comprises an adjuvant oily, an aqueous phase, at least one divalent inorganic salt, and at least one complexing agent.

The document CN108159414 describes a water-in-oil adjuvant for an animal vaccine and a method of preparation and application of the water-in-oil adjuvant. The water-in-oil adjuvant comprises the following raw materials by volume fraction: 74.5% to 76.5% Mineral Oil, 13.0% to 15.5% Span 80, 1.5% to 2.5% Tween 80, 2.5% to 3.0% Ester of Propylene glycol fatty acid, 2.5% to 3.5% hydroxylated lanolin, 1.5% to 2.0% glycerin monostearate, and 0.5% to 1.0% polyoxyethylene (2EO) oleyl alcohol ether. This document further discloses that the use of the described adjuvant provides a water-in-oil vaccine that is prepared by emulsification in a single step, the production process is simple, the cost is low, the water-in-oil vaccine obtained is safe and effective. It is low in viscosity, has few side effects, and has good stability.

The present invention is directed to a self-emulsionable mineral oil used as a vehicle in vaccines for the poultry industry, which has different advantages such as:
  Self-emulsionable mineral oil W/O (water in oil) useful at high and low temperatures.
  Possibility of emulsionable a higher antigenic load (percentage and type of immunogens).
  Lower density, which generates greater stability of the emulsion.
  The development of granulomas is eliminated.
  Shorter oil absorption time.
  There is a controlled release of one or more antigens found in the vaccine.
  Greater antigenic spectrum (polyvalent vaccines).
  Less undesirable post-vaccination reaction.
  Longer stability time to thermal variability.
  Greater resistance to mishandling of the biological (loss of the cold chain).
  Longer uptime of biological benefits, for example:
    Higher percentage of protection against field challenges.
    Higher antibody titer in serological tests.
    Greater possibility of using multipurpose vaccines.
    Longer stimulation time to the immune system.
    Immune response with longer protection time.
    No reactions after the application of vaccines.
    Much safer than attenuated virus vaccines.
    Best application in breeding animals, birds for egg laying and breeding.
    Increased immune response conferred by attenuated virus vaccines
    Longer expiration time, both for the manufactured vaccine and for the self-emulsionable mineral oil.
    Adequate stimulation of the immune system.

BRIEF DESCRIPTION OF THE FIGURES

For better understanding of the invention, a description of the same is provided below, together with the accompanying figure, in which.

DETAILED DESCRIPTION

Figure 1:
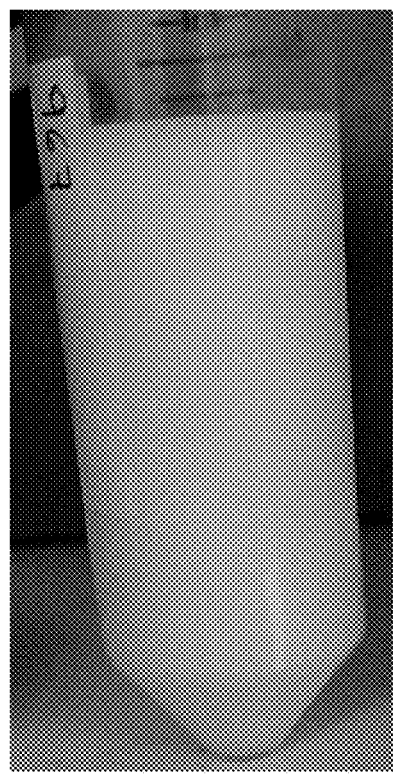
FIG. 1 shows the stability of the oil-in-water emulsion in a 60:40 ratio of self-emulsionable mineral oil within the scope of the present application, after 15 days at 36.5° C.
Figure 2:
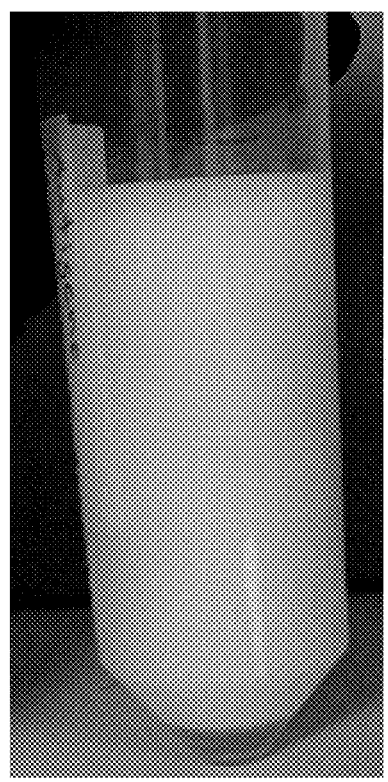
FIG. 2 shows the stability of the MONTANIDE® product in a 60:40 oil-in-water emulsion, after 15 days at 36.5° C.

The self-emulsionable mineral oil we speak about in the present application is a self-emulsionable mineral oil composed of mineral paraffinic oils and adjuvants.

Within the scope of the present application, paraffinic mineral oils are group II paraffinic mineral oils, which make up most of the final product, function as vehicle and adjuvant in the formulation of oily vaccines. Preferably, the paraffinic mineral oils used SN 60 and SN 35.

Along the same lines, within the scope of the present invention, adjuvants are categorized into water-in-oil (W/O) liquid emulsifiers and O/W (oil-in-water) emulsion stabilizers, as well as oil-in-water liquid emulsifiers (O/W) and O/W emulsion stabilizer (oil in water). Water-in-oil (W/O) liquid emulsifiers and O/W (oil-in-water) emulsion stabilizers are recommended for use with lipid components.

The preferred embodiment of the water-in-oil (W/O) liquid emulsifiers and O/W (oil-in-water) emulsion stabilizer are Sorbitan monooleate, (Z)-Sorbitan mono-9-octadecenoate (SPAN 80) and Mannide monooleate ([(3S,4S,5S,6R)-3,4,5-Trihydroxy-6-(hydroxymethyl)oxan-2-yl] (Z)-octadec-9-enoate) (CITHROL MMO).

Similarly, the preferred embodiment of the oil-in-water (O/W) liquid emulsifiers and the O/W (oil-in-water) emulsion stabilizer are (2-{2-[(2R,3R)-3,4-bis(2-hydroxyethoxy)oxolan-2-yl]-2-(2-hydroxyethoxy)ethoxy}ethyl dodecanoate) Polyoxyethylenesorbitan Trioleate(TWEEN 85) and Polyoxyethylene sorbitan oleate (TWEEN 81).

Self-emulsionable mineral oil is produced by placing the paraffinic mineral oils, namely SN 60 and SN 35, in a stirred container, shaking until a homogeneous mixture is obtained, without suspending stirring, on the homogeneous mixture adding the adjuvants, namely, SPAN 80, CITHROL MMO, TWEEN 85 and TWEEN 81, Polyglycerol Polyrricinoleate, PEG-30 dipolyhydroxystearate and continue stirring until a homogeneous mixture is obtained.

Self-emulsiionable mineral oil comprises the following specifications shown in the following Table 1:

TABLE 1

| PROPERTY | VALUE |
| --- | --- |
| * DENSITY AT 25° C. | 0.8367 |
| * VISCOSITY INDEX | 113 |
| * ACID NUMBER | 0.44 |
| * KINEMATIC VISCOSITY AT 100° C. | 2604 |
| * KINEMATIC VISCOSITY AT 40° C. | 9312 |
| VISUAL APPEARANCE | YELLOW AND TRANSPARENT |
| SAYBOLT COLOR | 6 |
| DYNAMIC VISCOSITY AT 20° C. | 15.46 |
| SAYBOLT VISCOSITY AT 100° F. | 58.68 |
| SAYBOLT VISCOSITY AT 210° F. | 35.02 |

In this sense, the mixing conditions are carried out in a time interval of 30 minutes, at 300 RPM, at room temperature, that is, between 20 and 25° C., and a hydrophilic-lipophilic balance (HLB) of 6.85.

The self-emulsionable mineral oil claimed in the present application provides greater stability at high and low temperatures in the W/O emulsion in a 40:60 and/or 30:70 ratio, that is, water with antigen:self-emulsionable mineral oil, therefore the Stages of the vaccine manufacturing process are reduced, since only the water will be dosed with the antigen (s) selected according to the vaccine to be produced, in the same way, when using the self-emulsionable mineral oil claimed in this application, a cost reduction is generated. in the final product.

Within the scope of the present application, the self-emulsionable mineral oil claimed in the present application is primarily intended for use in vaccines for the poultry industry, preferably for vaccines related to Newcastle disease, Influenza H2N5, bronchitis, salmonella, Infectious Bursal Disease (IBD), and hepatitis.

Additionally, it has been found that it is possible to emulsify a greater antigenic load, that is, percentage and type of immunogens, a lower density and viscosity is also obtained which does not cause granulomas or topical lesions, there is a controlled release of one or more antigens that are in the vaccine.

In this sense, once the vaccine was manufactured, that is, when mixed with the self-emulsionable mineral oil with antigen and other corresponding raw materials, a greater storage stability was found at 4, 24 and 37° C., as shown in the following Table 2:

TABLE 2

| EMULSION STABILITY | | |
|---|---|---|
| STORAGE AT 4° C. | STORAGE AT 25° C. | STORAGE AT 37° C. |
| MORE THAN 12 MONTHS | MORE THAN 6 MONTHS | MORE THAN 15 DAYS |

On this note, according to FIG. 1, the excellent stability shown by the self-emulsionable mineral oil in an oil-in-water (O/W) emulsion in a 60:40 ratio can be appreciated, after 15 days at 36.5° C., in which it is appreciated that the emulsion is in a single phase, despite having been subjected to a high temperature in terms of handling vaccines and/or antigen.

Unlike the aforementioned, according to FIG. 2, less stability can be seen that the MONTANIDE® product presents in an oil-in-water (O/W) emulsion in a 60:40 ratio, which was also subjected to 36.5° C. for 15 days. In FIG. 2, it can be seen that the emulsion already has two phases, which indicates that the high temperature and the combination of antigens at the 60:40 concentration affect the stability of the final product.

EXAMPLES

For the present application, field tests were performed on birds to evaluate and determine the favorable and unfavorable effects of the products manufactured with the reagents of the present invention. These tests were as follows:

Food safety test in broilers, parameters to be evaluated:

a.—Determine the macroscopic and microscopic lesions caused by the application of the vaccine in birds.

b.—Determine undesirable reactions in the growth and development of birds.

c.—Behavior or conduct of the birds after vaccination.

d.—Determine the collateral effect on weight gain as a consequence of vaccination.

Efficacy test

To comply with this test, the following was carried out:

a.—Determine the immune response by determining antibodies with the Hemagglutination Inhibition (HAI) technique for Newcastle virus (VNC).

b.—Rearing and fattening of the birds in field exposition, in the area of incidence of ENC.

Eight different formulations of emulsified vaccines against Newcastle disease (NDV), applied to 9-day-old broilers by subcutaneous route, were evaluated.

Birds in isolation housed in the facilities of the poultry company "Granjas Don Gil", located in Cuautla, Morelos.

180 1-day-old chicks of the Ross-368 line were used.

Feed to feed 180 chicks for 7 weeks of age (43 days post-vaccination)

8 bottles of 50 mL of each of the emulsified formulations in experimentation and commercial emulsified vaccine that was the control.

The Newcastle virus antigen with which the vaccines of the different batches were made was the inactivated Lasota strain with a titer of 109 DIEP50%/ml, (Acquired from Laboratorios Mayer S.A.) inactivated antigen to prevent Newcastle disease.

The required time was 43 days.

The 180 broiler chicks were randomly distributed in 9 groups of 20 birds, and each of the batches received one of the experimental formulas, the birds were identified with keys from each of the batches. The control group received the application of the commercial vaccine that the company uses for the prevention of Newcastle, according to the following table:

| LOTS |
|---|
| Lot 1, (VAP071220931EMU) |
| Lot 2, (VAP071220932EMU) |
| Lot 3, (VAP071220933EMU) |
| Lot 4, (VAP071220934EMU) |
| Lot 5, (VAP071220936EMU) |
| Lot 6, (VAP071220937EMU) |
| Lot 7, (VAP071220938EMU) |
| Lot 8, (VAP291220978EMU) |
| Lot 9, Control |

Lot 2 uses MONTANIDE® as a vehicle, Lot 3 uses DRAKEOL® as a vehicle, Lot 4 uses MARCOL® as a vehicle and Lot 5 uses SN 70 GII as a vehicle, while Lot 9 is the commercial vaccine.

All the birds received the same handling, feeding, treatments and accommodation. They were fed isoprotein and isoenergetic diets in three feeding stages (pre-initiation, initiation and completion) and free consumption of water.

All birds were vaccinated at 10 days of age against active Newcastle disease virus La Sota strain (Clone 30 from MSD Laboratories), with eye drop. Simultaneously, they were inoculated with the biologicals to be tested, applying 0.5 ml subcutaneously at the base of the neck. Immediately after the application of the product and every 24 hours, a report was kept on the behavior of the chickens, the injuries that occurred and the productive parameters.

After vaccination, macroscopic lesions and area of inflammation were determined, at 24 and 48 hours, 14 days and 21 days post-vaccination.

At 14 and 21 days post-vaccination, three chickens from each group were sacrificed and a necropsy was performed, the macroscopic and microscopic lesions caused by the treatments were determined and recorded.

Figure 3A:
FIGS. 3a and 3b show the area of application of the vaccine at 48 hours.
Figure 3B:
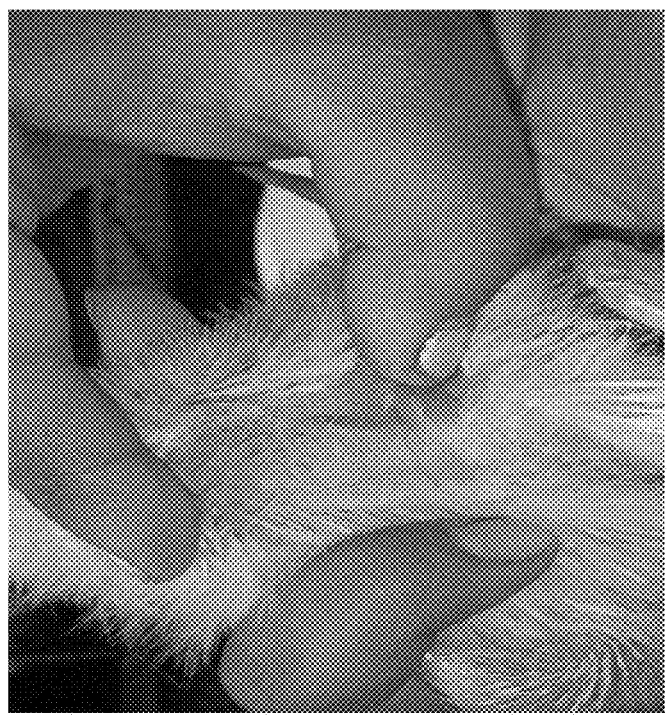

FIGS. 3a and 3b show the area of application of the vaccine at 48 hours, in which no apparent lesion is shown.

Figure 4A:
FIGS. 4a to 4c show the vaccine application area at 72 hours to chickens that were injected with the emulsified vaccine.
Figure 4B:
Figure 4C:

FIGS. 4a to 4c show the area of application of the vaccine at 72 hours to the chickens that were injected with the emulsified vaccine, in which the presence of the applied emulsion can be seen.

Figure 5:
FIG. 5 shows a chicken slaughtered at 48 hours where the presence of the vaccine is shown.

FIG. 5 shows a chicken slaughtered at 48 hours, in which the presence of the vaccine can be seen.

Figure 6:
FIG. 6 shows the necropsy of the neck of a vaccinated chicken with the emulsion from the experimental batch, sacrificed at 14 days.

FIG. 6 shows the necropsy of a chicken neck vaccinated with emulsion from the experimental batch, slaughtered at 14 days, in which it is possible to observe small accumulations of the vaccine covered by connective tissue without the presence of lesions such as hemorrhages, abscesses, granulomas or vaccine encapsulation.

Figure 7A:
FIGS. 7a and 7b show the area of application of the vaccine at 21 days to the chickens that were injected with the emulsified vaccine.
Figure 7B:

FIGS. 7a and 7b show the area of application of the vaccine at 21 days to the chickens that were injected with the emulsified vaccine, in which lesions, presence of granulomas, and much less abscesses were not observed.

For the determination of antibodies against Newcastle disease, 10 chickens from each of the 9 flocks were bled, puncturing the jugular vein to obtain 2 ml of blood without anticoagulant. These samples were taken at 21 days post-vaccination and finally at 35 days, the time the test ends (7.2 weeks of age). 3 chickens per batch were also slaughtered and tissue samples were taken from the application site. These samples were conserved and transported in a 10% formalin solution buffer and processed to perform the histopathological study to determine the possible microscopic damage attributable to the vaccine.

Jugular vein puncture blood samples were left at room temperature for 20 to 30 minutes, centrifuged in a clinical centrifuge at 2500 RPM for 10 minutes. Serum was obtained and stored frozen at −20° C. until use.

To determine the antibodies against ENC, the hemagglutination inhibition technique (IHA) described in NOM-052-ZOO-1995 was used and the samples were processed in the laboratory authorized by SAGARPA.

The histopathology and serology studies were carried out in a Laboratory approved by the zoo sanitary authorities and it is the "Cordobés Laboratory of Veterinary Diagnostic", which is located in Córdoba, Veracruz.

RESULTS

Safety Test.

No other changes were observed in the behavior of the birds in the trial, their behavior was normal and similar to the group of sister birds used in the fattening of the company.

There was no mortality in any of the animals in each of the batches.

The productive parameters such as feed consumption, weight gain, conversion index and productivity index were compatible with the expected parameters and specifications of the company's fattening flocks.

| LOT | Conversion | Productivity Index | Average weight | Mortality |
|---|---|---|---|---|
| 1 | 1.8 | 255 | 2.9 Kg | 0% |
| 2 | 1.8 | 257 | 2.95 Kg | 0% |
| 3 | 1.7 | 260 | 3.00 Kg | 0% |
| 4 | 1.8 | 258 | 2.89 Kg | 0% |
| 5 | 1.9 | 258 | 2.9 Kg | 0% |
| 6 | 1.8 | 259 | 2.95 Kg | 0% |
| 7 | 1.8 | 2.57 | 2.87 Kg | 0% |
| 8 | 1.82 | 260 | 3.1 Kg | 0% |
| 9.-Control | 2 | 247 | 2.85 Kg | 0% |
| Expected | 1.9 a 2 | 240 a 260 | 45 days/2.8 a 3.00 Kg. | 8 al 10% |

In some batches such as 1, 2, 3 and 8, the parameters were much better than those referred to and compared to the control batch, it is very important because this improves the productivity parameters and thus greater profit.

In the necropsy of the birds, no lesion or sign that was compatible with the inoculation of the product was found, no macroscopic lesions were observed, in the histopathological study only accumulation of heteroliphils and oil vacuoles were observed within the first 21 days after vaccination. However, in the last monitoring of the birds studied 35 days post-vaccination, the tissue did not show changes or lesions attributable to the inoculated product.

| AGE OF BIRDS Days | LOT 1-9 POST-VACCINATION TIME IN DAYS | Prostration | Wet Chicken | Bleeding zone | Cannibalism | Inflammation on the Application area | Necrosis | Mortality |
|---|---|---|---|---|---|---|---|---|
| 11 | 1st. | 2 hours | negative | negative | negative | light | negative | negative |
| 12 | 2nd. | negative | negative | negative | negative | light | negative | negative |
| 13 | 3rd. | negative | negative | negative | negative | light | negative | negative |
| 14 | 4th. | negative | negative | negative | negative | light | negative | negative |
| 15 | 5th. | negative | negative | negative | negative | negative | negative | negative |
| 16 | 6th. | negative | negative | negative | negative | negative | negative | negative |
| 17 | 7th. | negative | negative | negative | negative | negative | negative | negative |

-continued

| AGE OF BIRDS Days | LOT 1-9 POST-VACCINATION TIME IN DAYS | INJURIES OBSERVED | INJURIES OBSERVED |
|---|---|---|---|
| 12 | 2nd | 10:10 Presence of fatty matter (vaccine) | Not processed |
| 24 | 3rd. | 10:10 Formation of encapsulated material | 2:3 mononuclear and polymorphonuclear cells, 1:3 mononuclear |
| 35 | 4th. | 10:10 Presence of pearlescent fatty material of different sizes | Not processed |
| 36 | 5th. | 2:3 Presence of pearlescent fatty material of different sizes | 1:3 inflammatory reaction with the presence of vacuoles of encapsulated fat origin 2:3 small droplets of fatty material surrounded by a large number of polymorphonuclear cells |
| 43 | 6th. | 3:3 No apparent injuries | 3:3 No apparent changes |
| 44 | 7th. | 3:3 No apparent injuries | 3:3 No apparent changes |

The pathology studies of the samples sent to the laboratory showed inflammatory reactions in the area of application, it was only observed at the histopathology level. Macroscopically no harmful lesions were observed, only the vaccine. This was only observed within the first 14 days after vaccination. However, at the histopathological level, lesions compatible with the inflammatory process were found, as well as the absorption and processing of the oily material with the antigen under study, this was up to 21 days post-vaccination, a reaction that did not appear again in the samples. of those birds that were 43 and 44 days old and 35 to 36 days after vaccination, the time when the birds are sent to the market for human consumption.

These types of reactions and results are compatible with other results when other types of adjuvants are used, such as Aluminum Hydroxide Phosphate. However, this product is not enough to stimulate those immunological mechanisms that oil adjuvants perform and without causing injuries or altering the parameters of production and animal welfare.
Effectiveness Test.

For the second monitoring, which was 35 days post-vaccination and at the age of 45 days, time of sale and end of the production cycle, the results were variable in the trial lots. In some there is an increase up to 1:1028 and in others they decrease to 1:8.

The behavior per batch was:
The lots that were more stable are: 2, 3, 5, 6, 7 and 8 whose titles were from 1:8 to 1:128, for lots 1, 4 and 9 the titles are from 1:4 to 1:1028 and in general terms the titles suffered a decrease of up to 2 log.

When there is a decrease in the titers of antibody levels or these are heterogeneous, it may be due to the presence of immunosuppressive factors or infection with that infectious agent that reacts with the antibodies present, we can say that it is an active infection in this case with the NDV existence at the field level, (outbreak) without the animals used in the test showing signs of infection, much less lesions, only the serological evidence. This fact is relevant because it represents a challenge for the vaccinated birds which protected by not observing any sinology or behavior change of the animals, much less alteration of the productive parameters.

On the other hand, in lot 9 from the first monitoring, titers of 1:1028 appear, this lot was together with the rest of the flock and this one did present a slight respiratory condition throughout the fattening.

This problem is frequent, that is why birds are vaccinated and should not show any signs of disease when the vaccine protects.

Serology

First Monitoring.

| Day 1 | TITLES IHA | | | | | | | | |
|---|---|---|---|---|---|---|---|---|---|
| LOTS | 1:8 | 1:16 | 1:32 | 1:64 | 1:128 | 1:256 | 1:512 | 1:1024 | Average |
| 1 | — | 2/10 | 4/10 | 3/10 | 1/10 | — | — | — | 39.4 |
| 2 | — | 1/10 | 6/10 | 2/10 | — | — | — | — | 32.0 |
| 3 | — | — | 4/10 | 3/10 | 2/10 | 1/10 | — | — | 64.0 |
| 4 | 1/10 | 2/10 | 6/10 | 1/10 | — | — | — | — | 26 |
| 5 | — | 4/10 | 5/10 | 1/10 | — | — | — | — | 26.0 |
| 6 | 1/10 | 1/10 | 6/10 | 2/10 | — | — | — | — | 29.9 |
| 7 | — | 2/10 | 6/10 | 2/10 | — | — | — | — | 32 |
| 8 | — | — | — | 10/10 | — | — | — | — | 64 |
| 9 | — | — | 2/10 | 2/10 | 2/10 | 3/10 | — | 1/10 | 128 |

| | (14 days after) TITLES IHA | | | | | | | | |
|---|---|---|---|---|---|---|---|---|---|
| LOT | 1:8 | 1:16 | 1:32 | 1:64 | 1:128 | 1:256 | 1:512 | 1:1024 | Average |
| 1 | 3/10 | 3/10 | 1/10 | 3/10 | — | — | — | — | 19.7 |
| 2 | 3/10 | 5/10 | 2/10 | — | — | — | — | — | 32 |
| 3 | 1/10 | 6/10 | 1/10 | 2/10 | — | — | — | — | 21.1 |
| 4 | — | 3/10 | 1/10 | 3/10 | 2/10 | — | — | 1/10 | 59.7 |
| 5 | — | 3/10 | 5/10 | 2/10 | — | — | — | — | 29.9 |
| 6 | — | 4/10 | 5/10 | 1/10 | — | — | — | — | 26.0 |
| 7 | — | — | 4/10 | 4/10 | 1/10 | 1/10 | — | — | 59.7 |

| | | | | | | | | | |
|---|---|---|---|---|---|---|---|---|---|
| 8 | 2/10 | 2/10 | 6/10 | — | — | — | — | — | 21.1 |
| 9 | — | — | 1/10 | — | 4/10 | 2/10 | 2/10 | 1/10 | 207.9 |

CONCLUSIONS

The reagents and oils used are safe as they do not cause injuries or toxic or allergic reactions.

All the ingredients of the formula are properly absorbed in a timely manner.

The formula can be properly mixed with any inactivated microbiological agent used as an immunogen.

The immune system of birds is perfectly stimulated as a good adjuvant.

The degree of stimulation to the immune system allows and manages to maintain protection against field challenges.

Reduces production costs in manufacturing.

The present invention has been described in its preferred embodiment; however, it will be apparent to those skilled in the art that a multiplicity of changes and modifications can be made to this invention, without departing from the scope of the following claims.

The invention claimed is:

1. A self-emulsionable mineral oil, comprising mineral paraffin oils and adjuvants, wherein the adjuvants consist of: i) water-in-oil (W/O) liquid emulsifiers and oil-in-water (O/W) emulsion stabilizer; and ii) O/W liquid emulsifiers and O/W emulsion stabilizer;
   wherein i) consists of Sorbitan monooleate, (Z)-Sorbitan mono-9-octadecenoate and Mannide monooleate ([(3S,4S,5S,6R)-3,4,5-Trihydroxy-6-(hydroxymethyl)oxan-2-yl] (Z)-octadec-9-enoate); and
   wherein ii) consists of 2-{2-[(2R,3R)-3,4-bis(2-hydroxyethoxy)oxolan-2-yl]-2-(2-hydroxyethoxy)ethoxy}ethyl dodecanoate) Polyoxyethylenesorbitan Trioleate and Polyoxyethylene sorbitan oleate, Polyglycerol Polyricinoleate and PEG-30 dipolyhydroxystearate.

2. The self-emulsionable mineral oil according to claim 1, wherein the mineral paraffin oils are selected from SN 60 and SN 35.

3. The self-emulsionable mineral oil according to claim 1, wherein the self-emulsionable mineral oil is mixed with antigens and water, and wherein the water with antigens to self-emulsionable mineral oil are in a ratio of 40:60.

4. The self-emulsionable mineral oil according to claim 1, wherein the self-emulsionable mineral oil is mixed with antigens and water, and wherein the water with antigens to self-emulsionable mineral oil are in a ratio of 30:70.

5. The self-emulsionable mineral oil according to claim 1, wherein the self-emulsionable mineral oil has a storage stability time of 6 months at 25° C.

6. The self-emulsionable mineral oil according to claim 1, wherein the self-emulsionable mineral oil has a storage stability time of 15 days at 37° C.

7. The self-emulsionable mineral oil according to claim 1, wherein the self-emulsionable mineral oil has kinematic viscosity of 8 to 10.5 cSt at 40° C.

8. A method of producing the self-emulsionable mineral oil of claim 1, comprising: placing paraffinic mineral oils in a container with stirring; shake until a homogeneous mixture is obtained; without suspending stirring, adding the adjuvants into the homogeneous mixture; and continue stirring until a homogeneous mixture is obtained.

9. The method according to claim 8, wherein the paraffinic mineral oils comprise SN 60 and SN 35.

10. The method according claim 8, comprising mixing the self-emulsionable mineral oil with antigens and water so that the water with antigens to self-emulsionable mineral oil are in a ratio of 40:60.

11. The method according to claim 8, comprising mixing the self-emulsionable mineral oil with antigens and water so that the water with antigens to self-emulsionable mineral oil are in a ratio of 30:70.

12. The method according to claim 8, wherein stirring is carried out in a time interval of 30 minutes, at 300 RPM, at room temperature and a hydrophilic-lipophilic balance (HLB) of 6.85.

13. A poultry vaccine comprising the self-emulsionable mineral oil of claim 1 mixed with antigens.

14. A method for treating Newcastle disease, Influenza H2N5, bronchitis, *salmonella*, Infectious Bursal Disease (IBD), and hepatitis in poultry, comprising administering the poultry vaccine of claim 13 to the poultry.

* * * * *